US009789161B2

(12) United States Patent
Roy et al.

(10) Patent No.: US 9,789,161 B2
(45) Date of Patent: Oct. 17, 2017

(54) METHODS FOR TREATING BACK OR NECK PAIN CAUSED BY NGF USING A THERAPEUTIC AGENT CONSISTING OF REN-1820, ALE-0540 AND CAPSAICIN

(75) Inventors: Josee Roy, Germantown, TN (US); Susan J. Drapeau, Cordova, TN (US); Jeffrey C. Marx, Germantown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1595 days.

(21) Appl. No.: 11/414,689

(22) Filed: Apr. 28, 2006

(65) Prior Publication Data

US 2007/0253930 A1    Nov. 1, 2007

(51) Int. Cl.
| | | |
|---|---|---|
| *A61K 38/00* | (2006.01) | |
| *A61K 39/00* | (2006.01) | |
| *A61K 38/16* | (2006.01) | |
| *A61K 38/18* | (2006.01) | |
| *A61K 38/20* | (2006.01) | |
| *A61K 38/21* | (2006.01) | |

(52) U.S. Cl.
CPC ........ *A61K 38/1825* (2013.01); *A61K 38/185* (2013.01); *A61K 38/1858* (2013.01); *A61K 38/2093* (2013.01); *A61K 38/212* (2013.01)

(58) Field of Classification Search
CPC .. A61K 2300/00; A61K 38/179; A61K 38/18; A61K 38/185; A61K 9/0024; A61K 9/0085; A61K 31/225; A61K 31/00; A61L 27/34; A61L 31/10
See application file for complete search history.

(56) References Cited

U.S. PATENT DOCUMENTS

| | | | | |
|---|---|---|---|---|
| 5,147,294 A * | 9/1992 | Smith et al. | ................... | 604/500 |
| 5,876,762 A | 3/1999 | Collin | | |
| 6,028,066 A * | 2/2000 | Unger | ................ | A61K 41/0028 514/169 |
| 6,090,800 A * | 7/2000 | Unger | ................ | A61K 41/0028 514/180 |
| 6,120,751 A * | 9/2000 | Unger | ................ | A61K 41/0028 264/4 |
| 6,235,289 B1 * | 5/2001 | Aoki et al. | ................. | 424/236.1 |
| 6,403,056 B1 * | 6/2002 | Unger | ................ | A61K 41/0028 424/400 |
| 6,444,660 B1 * | 9/2002 | Unger | ................ | A61K 41/0028 514/180 |
| 6,455,567 B1 | 9/2002 | Monkhouse et al. | | |
| 6,468,990 B1 * | 10/2002 | Ross et al. | ...................... | 514/80 |
| 6,492,380 B1 * | 12/2002 | Ross et al. | .................... | 514/290 |
| 6,767,637 B2 * | 7/2004 | Park | ........................ | A61L 31/16 264/4.1 |
| 6,806,251 B2 * | 10/2004 | Lamb | ................ | 514/2 |
| 6,808,720 B2 * | 10/2004 | Unger | ................ | A61K 41/0028 424/450 |
| 6,919,426 B2 * | 7/2005 | Boone et al. | ................. | 530/322 |
| 7,148,352 B2 * | 12/2006 | Ross et al. | ...................... | 546/98 |
| 7,252,822 B2 * | 8/2007 | Shelton et al. | ............ | 424/145.1 |
| 7,255,860 B2 * | 8/2007 | Shelton et al. | ............ | 424/145.1 |
| 8,916,611 B2 * | 12/2014 | Roy | ........................ | A61K 31/11 514/576 |
| 2003/0054027 A1 * | 3/2003 | Unger | ................ | A61K 41/0028 424/450 |
| 2003/0082101 A1 * | 5/2003 | Taylor | ................ | A61K 41/0028 424/1.11 |
| 2003/0230819 A1 * | 12/2003 | Park | ........................ | A61L 31/16 264/4 |
| 2004/0038874 A1 | 2/2004 | Omoigui | | |
| 2004/0048370 A1 * | 3/2004 | Dennis et al. | ................ | 435/366 |
| 2005/0049195 A1 | 3/2005 | Zou | | |
| 2005/0147562 A1 * | 7/2005 | Hunter et al. | ................. | 424/9.5 |
| 2005/0197341 A1 | 9/2005 | Woolf et al. | | |
| 2005/0203206 A1 | 9/2005 | Trieu | | |
| 2005/0234425 A1 | 10/2005 | Miller et al. | | |
| 2005/0282774 A1 | 12/2005 | Eek | | |
| 2006/0046961 A1 * | 3/2006 | McKay | ................ | A61K 9/0085 424/85.1 |
| 2006/0083745 A1 | 4/2006 | Thorpe et al. | | |
| 2006/0263336 A1 * | 11/2006 | Caplan | ........................ | 424/93.7 |
| 2006/0282718 A1 * | 12/2006 | Perry et al. | .................... | 714/718 |
| 2007/0253928 A1 * | 11/2007 | Roy et al. | .................... | 424/85.2 |
| 2007/0253960 A1 * | 11/2007 | Roy et al. | .................... | 424/143.1 |
| 2007/0258938 A1 * | 11/2007 | Roy et al. | .................... | 424/78.3 |
| 2008/0097229 A1 * | 4/2008 | Roy et al. | .................... | 600/500 |

OTHER PUBLICATIONS

Burgess et al. J of Cell Bio. 111:2129-2138, 1990.*

(Continued)

*Primary Examiner* — Chang-Yu Wang

(57) ABSTRACT

The invention provides a method for alleviating discogenic pain by administering a therapeutic agent that disrupts neuronal and/or vascular elements in the disc, which is typically a degenerated disc. Disruption of neuronal elements in the disk includes destroying nerve endings without substantially affecting the central body of the nerve, suppressing activation of the nerve endings, and inhibiting the growth of nerve endings into the disk. Disruption of vascular elements includes causing the vascular extensions to retract from the disk, or suppressing the formation of such extensions. The therapeutic agent may be administered locally via an interbody pump, a bolus or a depot, or may be administered systemically.

14 Claims, 11 Drawing Sheets

(56) References Cited

OTHER PUBLICATIONS

Bowie et al. Science, 1990, 247:1306-1310.*
Pawson et al. 2003, Science 300:445-452.*
White et al. Nat Rev. Drug discovery. 2005. 4: 834-844.*
Wang et al. Adv. Drug Delivery Rev. 2003. 55:949-965.*
Joshua et al. J. Pharmacol. Exp. Thera. 1999. 289:1271-1276.*
Djouhri et al. J. Neurosci. 2001, 21: 8722-8733.*
The News from the University of Bristol published on Nov. 16, 2005, from the internet: http://www.bristol.ac.uk/news/2005/11321608504, retrieved on Jan. 4, 2009.*
Watson et al. (J. Pharmacol.Exp. Ther., Mar. 2006. 316: 1122-1129).*
An intervertebral disk image retrieved from the MedlinePlus Medical Encyclopedia website (retrieved on Jul. 31, 2009 from http://www.nlm.nih.gov/medlineplus/ency/imagepages/19469.htm).*
Kuiper et al. SPINE, 1998, 23: 657-663.*
Kairemo et al., J. Nucl. Med. 2001; 42: 476-482.*
Owolabi et al. J. Pharmacol. And Exp. Thera. 1999; 289:1271-1276.*
Klibanov Invest. Radiol. 2006; 41:354-362.*
Teng, et al., "Adenoviral clostridial light chain gene-based synaptic inhibition through neuronal synaptobrevin elimination.", *Gene Therapy*, (2005) 12, 108-119.
Kairemo, et al., "In Vivo Detection of Intervertebral Disk Injury Using a Radiolabeled Monoclonal Antibody Against Keratan Sulfate.", *The Journal of Nuclear Medicine*, 42(3), (Mar. 2001), 476-482.
Subin, et al., "Treatment of Chronic Low Back Pain by Local Injection of Botulin.", *The Internet Journal of Anesthesiology.* 6(2), (2003), 1-8.
Unknown, "Anti-angiogenesis: Next Era of Cancer Therapy Aims to Separate Cancer From Blood Supply.", *M.D. Anderson Cancer Center*, (Mar. 14, 2006), 1-3.
Klibanov, "Targeted Imaging and Ultrasound-Assisted Drug-Delivery Applications.", *Investigative Radiology*, 41(3), (Mar. 2006), 354-362.
Unknown, "Innervation of 'Painful' Lumbar Discs.", *Spine*, 22(20), (Oct. 15, 1997), 37-49.
Cornelia, et al., "Why do intervertebral discs degenerate?", *Eurodisc*, 1-10.
Gingras, et al., "Shark cartilage extracts as antiangiogenic agents: Smart drinks or better pills?", *Cancer Metathesis Review*, 19(1-2), (2000), 83-86.
Patacchini, et al., "Capsaicin-like activity of some natural pungent substances on peripheral endings of visceral primary afferents.", *Naunyn Schmiedebergs Arch Pharmacol.*, 342(1), (Jul. 1990), 72-77.

Sawynok, et al., "Topical and Peripherally Acting Analgesics.", *Pharmacological Reviews* 55(1), (2003), 1-20.
Melrose, et al., "Increased Nerve and Blood Vessel Ingrowth Associated With Proteoglycan Depletion in an Ovine Anular Lesion Model of Experimental Disc Degeneration.", *Spine*, 27(12), (2002), 1278-1285.
Aoki, et al., "Neuropathology of Disgenic Low Back Pain: A Review." *The Internet Journal of Spine Surgery*, 2(1), (2005), 1-15.
Manchikanti, et al., "Evidence-Based Practice Guidelines for Interventional Techniques in the Management of Chronic Spinal Pain.", *Pain Physician*, 6(1), (2003), 1-81.
Martin, et al., "Pathophysiology of Lumbar Disc Degeneration: A Review of the Literature.", *Neurosurg Focus*, 13(2), (Oct. 15, 2002), 1-11.
Stylli, et al., "Photodynamic therapy of cerebral glioma—A review Part II—Clinical studies.", *Journal of Clinical Neuroscience*, (Nov. 2005), 1-9.
Knight, et al., "Non-viral neuronal gene delivery mediated by the HC fragment of tetanus toxin.", *Eur. J. Biochem.*, 259(3), (Feb. 1999), 762-769.
Box, et al., "A multi-domain protein system based on the HC fragment of tetanus toxin for targeting DNA to neuronal cells.", *Journal of Drug Targeting*, 11(6), (Aug. 2003), 333-343.
Wallach, et al., "Safety assessment of intradiscal gene transfer: a pilot study.", *The Spine Journal 6*, (May 2005), 107-112.
Allen, et al., "Safety Evaluation of Intrathecal Substance P-Saporin, a Targeted Neurotoxin, in Dogs.", *Toxicological Sciences*, 91(1), (2006), 286-298.
Olmarker, et al., "Neovascular and Neoinnervation of Subcutaneously Placed Nucleus Pulposus and the Inhibitory Effects of Certain Drugs.", *Spine*, 30(13), (2005), 1501-1504.
Unknown, "Vanilloid Receptor Research Tools: Cell Signaling and Neuroscience.", *Sigma-Aldrich*, (2006), 1-2.
Zhang, et al., "Group I Metabotropic Glutamate Receptor Antagonists Block Secondary Thermal Hyperalgesia in Rats with Knee Joint Inflammation.", *Pharmacology and Experimental Therapeutics*, 300(1), (Jan. 2002), 149-156.
Johnson, et al., "Human Intervention Disc Aggracan Inhibits Endothelial Cell Adhesion and Cell Migration In Vitro.", *Spine*, 30(10), (May 15, 2005), 1139-1147.
Cameron, et al., "A Prospective Study of Serum Pseudo cholinesterase Levels in Patients With Chronic Spinal Pain.", *Spine*, 25(15), (2000), 1917-1924.
Watson, et al., "TrkAd5: A Novel Therapeutic Agent for Treatment of Inflammatory Pain and Asthma", *The Journal of Pharmacology and Experimental Therapuetics*, 2006, vol. 316, No. 3, 1122-1129.
Nickel, et al., "Changing Paradigms for Chronic Pelvic Pain", MedReviews, LLC, Oct. 19-21, 2005, Baltimore, MD, Reviews in Urology, vol. 8 No. 1 2006, 28-35.

* cited by examiner

METHODS FOR TREATING BACK OR NECK PAIN CAUSED BY NGF USING A THERAPEUTIC AGENT CONSISTING OF REN-1820, ALE-0540 AND CAPSAICIN

FIELD OF THE INVENTION

The present invention relates to systems and methods for decreasing or eliminating neck or back pain. More specifically, the invention relates to methods and related systems for administering a therapeutic agent that destroys, disrupts or causes retraction of neuronal and/or vascular extensions in a degenerating disc. The contemplated methods may comprise administration of such therapeutic agent alone or in combination with an anti-inflammatory, anesthetic and/or analgesic agent(s).

BACKGROUND OF THE INVENTION

In a Gallup Survey, 42% of American adults said that they experienced pain on a daily basis. Amongst such sufferers of chronic pain, spine-related problems constitute the bulk of the complaints. Spinal pain has been estimated to exist in as much as 66% of the general population. Beyond the substantial discomfort that back pain inflicts upon individuals, spine-related pain also incurs heavy social costs. For example, as many as one million spine surgeries, and as many as five million interventional procedures, are estimated to be performed in the United States each year. Well beyond the purely medical and psychological burdens of such procedures, the subsequent social costs related to productivity, disability compensation, and lost taxes, are substantial.

Currently, one of the most common treatments for discogenic pain is the removal of the disc associated with the pain; the adjacent vertebrae are then fused together, using either bone grafts, mechanical implants, or a combination of the two. This is drastic, highly invasive surgery that is both expensive and problematic. In particular, recovery times range from six months to over a year, and as many as 50% of patients experience subsequent pain levels to a degree that is equal to, or even exceeds, their pre-surgery levels.

It is therefore desirable to provide other methods of reducing discogenic-related pain that is both less costly and less surgically extreme.

SUMMARY OF THE INVENTION

In one aspect of the invention, a method for treating discogenic pain is provided that includes administering an effective amount of a therapeutic agent to a disc, in which the therapeutic agent is adapted to disrupt neuronal elements in the disc, or in a region around the disc. In another aspect, the therapeutic agent is adapted to disrupt vascular elements in the disc or a region around the disc. In another aspect, the therapeutic agent comprises an active ingredient linked to a molecule that can interact with a neuronal element or an element of the degenerative disc. In another aspect, the therapeutic agent is adapted to modulate a receptor or a molecule that binds to a receptor of the neuronal element innervating the disc region. The disc may be, for example, a degenerated disc, and the neuronal or vascular elements may both be within the disc, on the outer surface of the disc, or in a region that includes about 5 cm around the disc. The neuronal or vascular elements may also lie within the inner two thirds of the annular fibrosus of the disc, or may be within the nucleus pulposus of the disc. Disruption of the neuronal elements can include, for example, suppression or reduction of the sensitivity or activity of the neuronal elements, prevention of the formation or further growth of such elements, and retraction or destruction of neuronal extensions while leaving the central neuronal components substantially intact. Disruption of the vascular elements may include prevention of the formation or further growth of such vascular elements, inducing retraction of the vascular elements, or destroying the vascular elements.

In one embodiment, the therapeutic agent is adapted to destroy, force retraction or block the further growth of the neuronal elements in the disc or disc region. In a particular embodiment, the therapeutic agent comprises a neurotoxin and cell membrane-permeabilizing agents, which may be, for example, a natural compound, a synthetic compound, a dye, saponins or saporin.

In another embodiment, the therapeutic agent is designed to modulate at least one growth factor, or the response of the neuronal elements to a growth factor. Exemplary growth factors include nerve growth factor, brain-derived growth factor, glial-derived growth factor, neurotrophin-3, neurotrophin-4, insulin-growth factor, fibroblast growth factor and leukemia inhibitory factor. Exemplary active ingredients include ALE-0540 and ReN-1820.

In yet another embodiment, the therapeutic agent is adapted to modulate an extra-cellular matrix component, or to modulate the response of the neuronal elements to an extra-cellular matrix component. Exemplary extra-cellular matrix components include chondroitin sulfate proteglycans, netrins, semaphorins and myelin/oligodendrocyte growth inhibitors, such as Nogo, MAG and Omgp. Alternatively, the extra-cellular matrix component may be a cell adhesion molecule, such as NCAM, N-cadherins and integrins. As an exemplary active ingredient, Semaphorin III protein can repulse sensory neuronal extensions that are invading a site of injury and inflammation. See D. L. Tanelian et al., *Semaphorin III can repulse and inhibit adult sensory afferents in vivo*, 3(12) NAT. MED. 1398-401 (1997). Function-blocking anti-integrin antibodies that can reduce the development of hyperalgesia may also serve as suitable active ingredients. See O. A. Dina et al., *Primary afferent second messenger cascades interact with specific integrin subunits in producing inflammatory hyperalgesia*, 115(1-2) PAIN 191-203 (2005).

In another embodiment, the therapeutic agent is adapted to modulate a cytoskeletal component, or the organization of established or actively growing neuronal elements. Exemplary cytoskeletal components may include actins, tubulins or neurofilaments, and an exemplary active ingredient for the therapeutic agent may be a Rho kinase activator. Cytotoxic necrotizing factor-1 and -2 from *E. coli* may be suitable Rho kinase activators.

In one embodiment, the therapeutic agent is adapted to desensitize the neuronal elements in the disc or disc region. Various specific embodiments include selecting an active ingredient for the therapeutic agent, such as camphor, menthol, piperine, mustard oil, curcumin and eugenol. Other embodiments include the use of a vanilloid receptor agonist for the active ingredient, such as 8-Methyl-N-vanillyl-trans-6-nonenamide (Capsaicin); Z-Capsaicin; Gingerol; Zingerone; 8-Methyl-N-vanillylnonanamide (Dihydrocapsaicin); 6,7-Deepoxy-6,7-didehydro-5-deoxy-21-dephenyl-21-(phenylmethyl)-daphnetoxin,20-(4-hydroxy-5-iodo-3-methoxybenzeneacetate) (5'-Iodoresiniferatoxin)-?; (+)-Isovelleral; N-Vannilyloleoylamide (Olvanil); Phorbol 12,13-dinonanoate 20-homovanillate; Resiniferatoxin; N-(3-Methoxyphenyl)-4-chlorocinnamide (SB-366791); 2,3,4-Trihydroxy-6- methyl-5-[(2E,6E)-3,7,11-trimethyl-2,6,10-dodecatrienyl] benzaldehyde (Scutigeral); 6,7-Deepoxy-6,7-didehydro-5-deoxy-21-dephenyl-21-(phenylmethyl)-20-(4-hydroxybenzeneacetate)daphnetoxin (Tinyatoxin); capsaicin synthetics; and capsaicin derivatives.

In another embodiment, the therapeutic agent is adapted to modulate the neuronal elements in the disc. In a specific embodiment, the therapeutic agent modulates the activity of the neuronal elements innervating the disc or disc region. For example, the therapeutic agent may modulate neuronal receptors, such as nociceptors, vanilloid, adrenergic, cholinergic, glutamate, GABA, serotonine, somatostatin opioids, ATP, Na+, K+, Ca2+, cannabinoids, Substance P and neuropeptide receptors; suitable active ingredients may include botulinum toxin, anti-convulsants, anesthetics, analgesics, opioids and cannabinoids. Other suitable active ingredients include vanilloid receptor antagonists, such as N-[2-(4-Chlorophenyl)ethyl]-1,3,4,5-tetrahydro-7,8-dihydroxy-2H-2-benzazepine-2-carbothioamide (Capsazepine); [N-(4-Hydroxy-3-methoxyphenyl)methyl]-5Z,8Z,11Z,14Z-eicosatetraenamide] (Arvanil); N-(3-Methoxyphenyl)-4-chlorocinnamide (SB-366791) and 5'-iodoresiniferatoxin.

In another embodiment, the therapeutic agent may cause reduction in the sensitization of the neuronal elements by a pro-inflammatory molecule. Exemplary pro-inflammatory molecules include cytokines, chemokines, neuropeptides, bradykinin, histamine and prostaglandins. Suitable active ingredients may include steroids, nonsteroidal anti-inflammatory drugs, COX inhibitors, modulators of TNF-alpha or IL-1 cytokine levels or receptors, or NFkB modulators.

In yet another embodiment, the therapeutic agent is adapted to modulate glial cells. In specific embodiments, the therapeutic agent comprises fluorocitrate or minocyclin.

In another aspect, the therapeutic agent is adapted to disrupt vascular elements in the disc or disc region. The active ingredient within the therapeutic agent may include, for example, an anti-angiogenic agent, or a cell membrane-permeabilizing agent like saporin.

In another embodiment, the therapeutic agent is adapted to modulate a growth factor or cytokine, or the response of the vascular element to a growth factor or cytokine. The growth factor or cytokine may be, for example, vascular growth factor, fibroblast-growth factor, angiopoietins, pigment epithelium-derived factor or α-IFN.

In yet another embodiment, the therapeutic agent may comprise an inhibitory antibody, aptamer, or a soluble fragment of a growth factor or growth factor receptor. Examples include bevacizumab, pegaptanib and ranibizumab.

In another embodiment, the therapeutic agent may comprise an anti-angiogenic steroid or an angiostatic steroid, such as anecortave acetate or triamcinolone acetonide.

In another embodiment, the therapeutic agent modulates an extra-cellular matrix component or the response of the vascular element to an extra-cellular matrix component. The extra-cellular matrix component may be an MMP inhibitor, such as marimastat. Alternatively, the extra-cellular matrix component may be a cell adhesion molecule, such as cadherins or integrins.

In yet another embodiment, the therapeutic agent modulates a cytoskeletal component of established or actively growing vascular extensions, such as microtubules. Suitable active ingredients may include combretastatin, vinca alkaloid or placlitaxel.

In another embodiment, the therapeutic agent may modulate the response of vascular elements to pro-inflammatory molecules. Exemplary pro-inflammatory molecules include cytokines, chemokines, neuropeptides, bradykinin, histamine and prostaglandins. Suitable active ingredients may include steroids, nonsteroidal anti-inflammatory drugs, COX inhibitors, modulators of TNF-alpha or IL-1 cytokine levels or receptors, or NFkB modulators.

In certain embodiments, two or more active ingredients may be selected to form the therapeutic agent, each active ingredient being selected to perform one or more of the embodiment aspects indicated above. For example, the therapeutic agent may comprise one active ingredient that destroys, forces the retraction or blocks the further growth of the neuronal elements, another active ingredient that desensitizes or modulate the activity of the neuronal elements in the disc or disc region, and yet another active ingredient that disrupts the vascular extensions.

The therapeutic agent may be administered locally. In one embodiment, the therapeutic agent has a targeted release rate, and is injected as a bolus in, or near to, the disc. In another embodiment, a controlled administration system releases the therapeutic agent. The controlled administration system may be, for example, a depot, an infusion pump, an osmotic pump, or an interbody pump. The controlled administration system may be implanted in, or near, the disc. In a specific embodiment, the controlled administration system comprises a catheter in or near the disc, the catheter having a proximal end and a distal end, the distal end having an opening to deliver the therapeutic agent in situ, the proximal end being fluidly connected to a pharmaceutical delivery pump.

In another aspect, the invention discloses systemic targeted delivery of the at least one active ingredient by delivering a pharmaceutical composition comprising an antibody to a marker of a degenerated disc, conjugated with one or more active ingredients. In one embodiment of the invention, the marker of the degenerated disc is keratin sulfate. The antibody may be monoclonal.

In yet another aspect, the therapeutic agent comprises an active ingredient linked to a molecule that binds to, or is incorporated by, the vascular or neuronal element. The molecule may be, for example, a growth factor, or an antibody or peptide capable of interacting with the neuronal or vascular element.

In another embodiment the therapeutic agent or the active ingredient is activated by light, and the invention method may further comprise illuminating the disc region with light of a suitable wavelength that activates the therapeutic agent.

In yet another embodiment, the therapeutic agent may comprise one or more active ingredients encapsulated by microbubbles. The method may further comprise delivering sonic energy to the disc region. The sonic energy is of a suitable frequency and intensity that causes the microbubbles to release the active ingredient or ingredients.

In yet another embodiment, the therapeutic agent or active ingredient is encoded by a synthetic or natural gene sequence, wherein the active ingredient is delivered to a degenerated disc via targeted gene therapy.

DETAILED DESCRIPTION

Figure 1A:
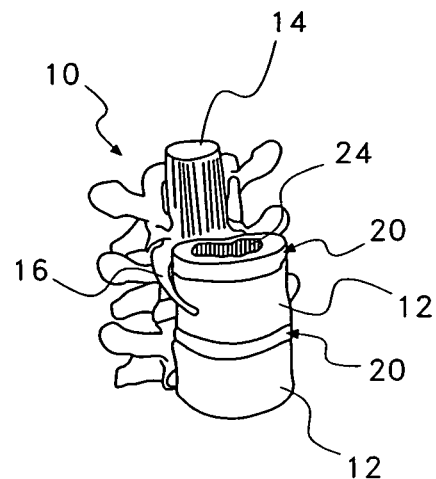
FIG. 1A is an anterior perspective view of a spine.
Figure 1B:
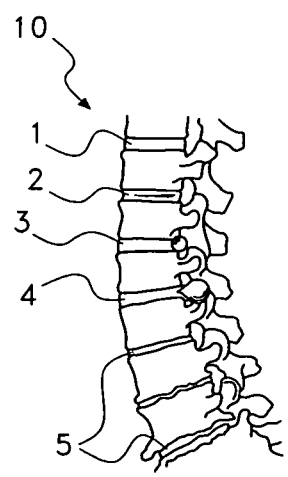
FIG. 1B shows a spine with normal and degenerated discs.
Figure 2:
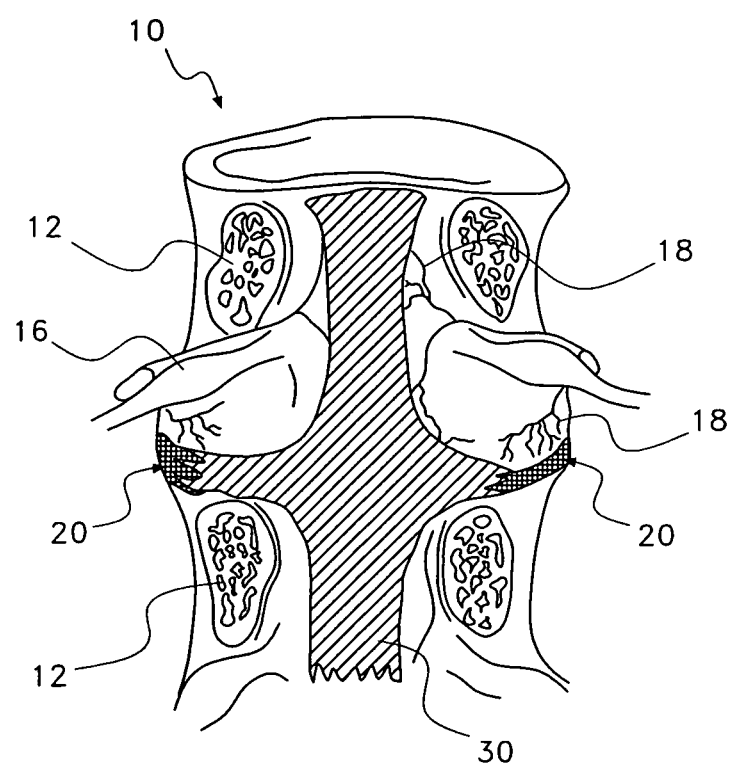
FIG. 2 is a posterior perspective view of a spine.
Figure 3:
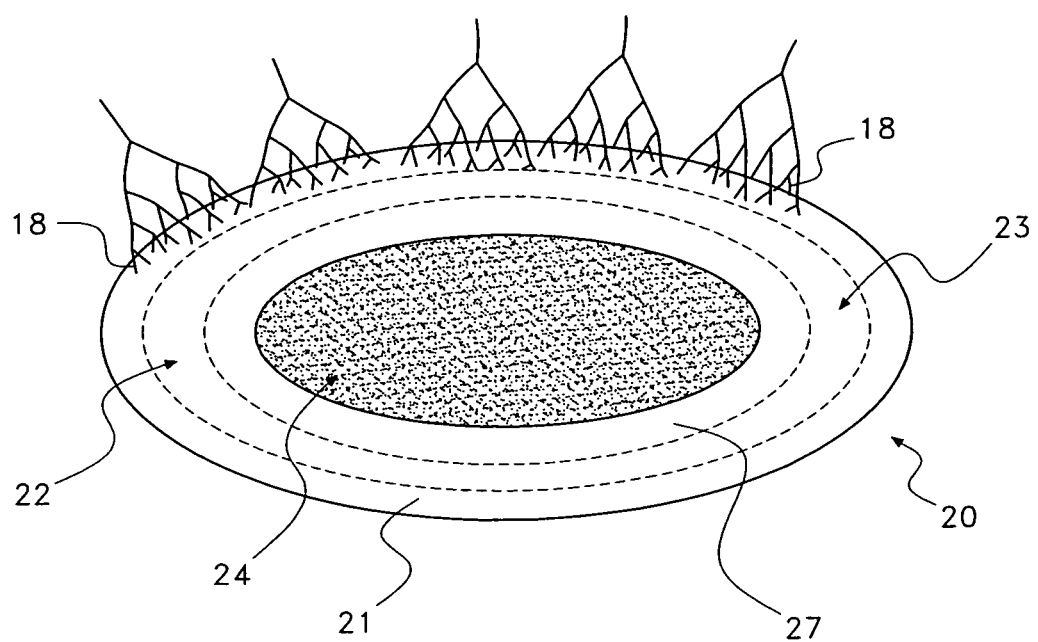
FIG. 3 shows neuronal extensions penetrating centripetally into a disc.

The spine is a remarkably strong and flexible structure that is capable of withstanding substantial forces. As shown in FIGS. 1-3, a spine 10 is formed from a plurality of vertebrae 12, each of which is individually separated from the other by a disc 20. The discs 20 abut the spinal cord 14, which runs through the spinal canal of the vertebrae 12. The discs 20 have several functions, one of which includes serving as shock absorbers for the vertebrae 12.

Each disc 20 is somewhat like a jelly donut, having a relatively tough outer layer called the annulus fibrosus 22 that surrounds a gel-like inner layer called that nucleus pulposus 24. The annulus fibrosis 22 is composed of concentric layers of intertwined annular bands, which are arranged to resist forces placed upon the spine 10. The cartilaginous endplate, adjacent to the disc 20, separates the nucleus pulposus 24 and annulus fibrosus 22 from the adjacent vertebrae 12. The posterior longitudinal ligament 30 strongly attaches to the annulus fibrosus 22. The nucleus pulposus 24 is composed of cells from the primitive notochord, and contains significant amounts of substances capable of exciting, or increasing the excitability of, sensory nerves. These substances include prostaglandin E, histamine-like substances, potassium ions, lactic acid, and several polypeptide amines.

Pain arising from the disc 20 may be termed discogenic pain. Generally, though not always, to experience pain in a particular region the presence of nerve endings in that region is required. One source of pain is caused by the activation of specific nociceptors connected with C- and A-delta fibers. Another source of pain involves injury to sensory fibers, or damage to the central nervous system. Hence, the innervation of the disc 20 is of interest to the study of discogenic pain.

Branches 16 extend from the spinal cord 14, with sub-branches 18 innervating the disc 20. A meningeal branch 16 of the spinal cord 14, termed the recurrent sinuvertebral nerve, innervates the area around the disc 20. Exiting from the dorsal root ganglion and entering the foramen, the sinuvertebral nerve 16 divides into major ascending and lesser descending branches. As shown in FIG. 3, the branches 18 generally innervate only the outer third 21 of the annulus fibrosus 22, and hence typically do not enter into the inner two thirds 23 of annulus fibrosus 22, nor into the nucleus pulposus 24.

The discs 20 are surrounded by the interlacing nerve fibers 18. Although the nerve fibers 18, including the sinuvertebral nerve 16, are related to structures generally considered sympathetic, this does not necessarily mean that the nerve fibers 18 are fully sympathetic in function. Most such nerves 18 may have a sensory function. Moreover, the sympathetic nervous system is capable of interacting with sensory C-fibers, which are sensitizing nociceptors, thereby inducing further sympathetic activity in the spinal cord 14. Studies have demonstrated the presence of sensory fibers in the discs 20 of humans; substance P(SP) and calcitonin gene-related peptide (CGRP)-immunoreacitive (-IR) nerve fibers are also present in the disc 20. Because SP and CGRP are both expressed in nociceptive neurons and their axons, these SP- and CGRP-IR nerve fibers 18 within the disc 20 are thought to be involved in transmitting nociceptive information from the disc 20. Hence, the disc 20 itself can be a source of pain.

Normal discs 20 are rarely innervated deeper than the outer third 21 of the annulus fibrosus 22. However, there are indications that degenerated or problematic discs 20 have nerve extensions 18 that extend centripetally beyond the outer third 21 of the annulus fibrosis 22, reaching as far as the inner third 27 of the annulus fibrosis 22, or even into the nucleus pulposus 24. The invasion of such neuronal extensions 18 may be a source of pain, particularly if they come into contact with those substances in the nucleus pulposus 24 that are capable of exciting such neuronal extensions 18. Back and neck pain can be caused by a degenerated disc. A degenerated disc 20 may, but not necessarily always, show anatomical signs of degeneration, which can include changes in the height of the disc 20, the level of hydration of the disc 20, annular bulging, or the presence of tearing or osteophytes. A reduction in the height of the disc 20 may be one of the most common, early and easily detectable changes present in a degenerated disc. Another sign of degeneration is normally loss of the T2 weighted signal on an MRI scan; this is indicative of a loss of hydration of the nuclear tissue. The disc 20 may be any disc within a spinal column, including cervical, thoracic and lumbar discs. Specific reference is drawn to FIG. 1B. A normal disc 1 is shown in a spinal column 10, along with other degenerated discs 2-5. The degenerated disc can be a contained disc 5 that simply shows signs of thinning, or a herniated disc 3, 4. Herniation could be of a contained nature called, for example, bulging of the disc, as shown by disc 3. A herniated disc can also be ruptured with release of discal elements, such as the nucleus pulposus 24, outside the disc, as shown by disc 4. As shown by disc 2, a degenerated disc may also show signs of tearing. A bulging disc 3 or ruptured, herniated disc 4 can apply a pressure on the nerve roots 16 and cause radicular pain or radiculopathy. Radiculopathy refers to disease of the spinal nerve roots (from the Latin radix for root).

Radiculopathy produces pain, numbness, or weakness radiating from the spine. Radiculopathies are categorized according to which part of the spinal cord is affected. Thus, there are cervical (neck), thoracic (middle back), and lumbar (lower back) radiculopathies. Lumbar radiculopathy is also known a sciatica. Radiculopathies may be further categorized by what vertebrae they are associated with. For example, radiculopathy of the nerve roots at the level of the seventh cervical vertebra is termed C7 radiculopathy; at the level of the fifth cervical vertebra, C5 radiculopathy; at the level of the first thoracic vertebra, T1 radiculopathy; and so on.

Figure 4:
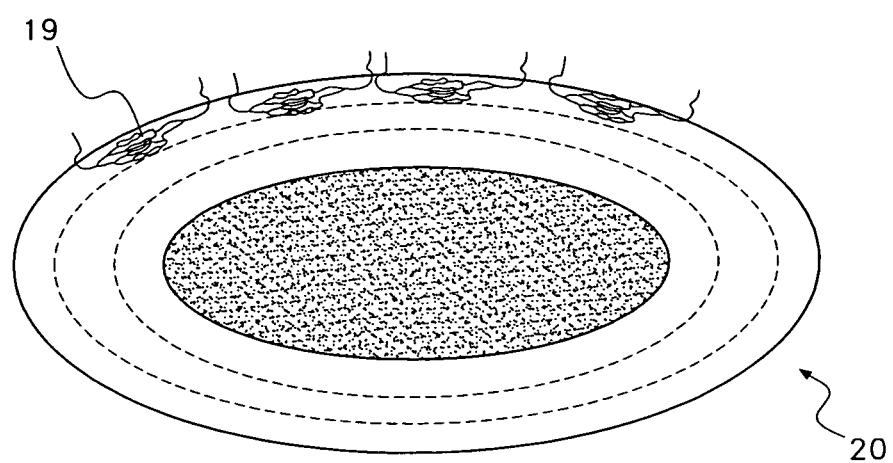
FIG. 4 shows vascular extensions in a disc.

Discs 20 are generally avascular, with the transport of nutrients and metabolites occurring primarily through diffusion. However, with further reference to FIG. 4, degenerated discs 20 tend to be more vascular than normal discs 20. This centripetally invasive vascularization 19 of the disc 20, analogous to the neuronal invasion 18 depicted in FIG. 3, may contain a perivascular nerve network with vasomotor or vasosensory functionalities. Further, increased vascularization of the disc 20 may be associated with increased innervation, and hence increased chances for discogenic pain.

Figure 5:
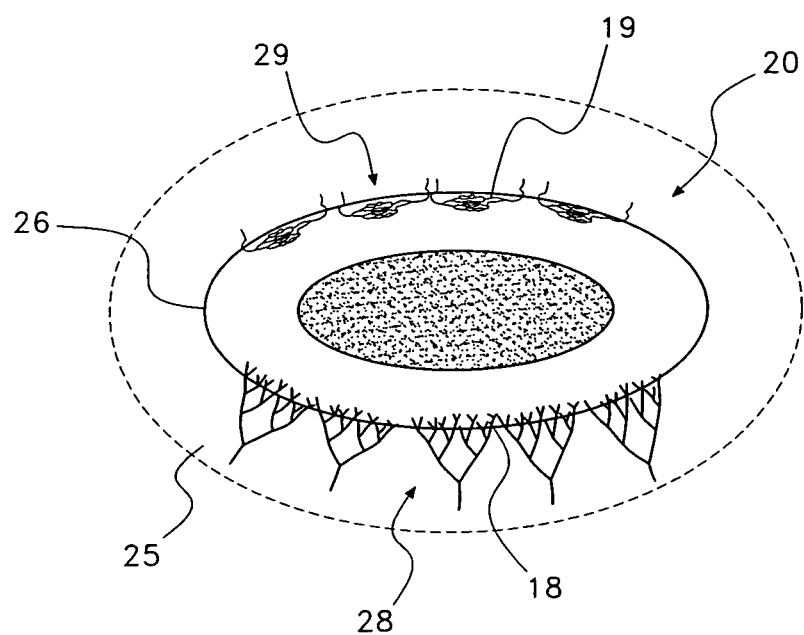
FIG. 5 shows a disc region that includes a disc having centripetally invasive neuronal and vascular extensions and associated elements.

With reference to FIG. 5, and without wishing to be bound by theory, it is believed that invasion of the disc 20 by neuronal extensions 18 or vascular extensions 19 may be a source of discogenic pain. The current invention provides systems and methods for decreasing, eliminating, or managing discogenic pain by providing a therapeutic agent that disrupts neuronal elements 28 and/or vascular elements 29 in a disc region 25. The disc region 25 includes the disc 20 that is believed to be a source of pain. Such discs 20 are typically degenerated discs. The disc region 25 may extend as far as 5 cm from the outer surface 26 of the disc 20. A therapeutic agent may be on a continuum from rapid acting to long acting. The therapeutic agent has at least one active ingredient, and can range in a continuum from rapid release to sustained release. Still further, the delivery of the therapeutic agent via controlled administration can include, for example, rapid and repeated delivery at intervals, or continuous delivery. The delivery can be localized, or may target the disc region 25, and in particular, may target the disc 20.

As used herein, a therapeutic agent is a medicinal composition designed to achieve a medically useful end. A therapeutic agent typically comprises at least one active ingredient, alone or as part of, on, with, within or complexed with a depot, and optionally diluents, excipients and other pharmaceutically acceptable agents desirable for improved stability, manufacturing, efficacy and the like. As used herein, an active ingredient is a disruptor of neuronal or vascular elements in a disc region. The term "in a disc region" is intended to include a region extending about 5 cm from the surface of a disc, the surface of the disc, as well as interior regions within the disc. The term "disc" is intended to include any disc within a spinal column that separates individual vertebrae from each other, such as cervical, thoracic or lumbar discs. Application of the therapeutic agent causes disruption of neuronal elements in the disc region, vascular elements in the disc region, or both. A "neuronal element" includes a neuron body; extensions of a neuron, such as axons, axonal branches, dendrites or growth cones; and supporting cells, such as glial cells including astrocytes, Schwann cells and microglia. The one or more active ingredients in the therapeutic agent may achieve disruption of neuronal elements by reducing or suppressing activation of the neuronal elements, preventing or reducing the formation of such neuronal elements in the disc region, or destroying, inducing retraction or modulating further growth of the neuronal elements already present in the disc region. A "vascular element" includes blood vessels, capillaries and endothelial cells. The one or more active ingredients may achieve disruption of vascular elements by preventing the formation of such vascular elements, causing the retraction of the vascular elements from the disc region, or causing the destruction of the vascular elements. Disruption of an element may also be obtained by modulating an aspect of that element. In the following, to "modulate" an aspect of an element, be it a neuronal or vascular element, is intended to mean to affect the activity, concentration, number of or level of that aspect of the element. Disruption of an element in the disc region does not necessarily mean that the element is disrupted in the entire disc region; rather, this may also mean that the element is disrupted in at least a portion or subset of the disc region, such as within the disc, or within an internal region of the disc.

As indicated above, excipients may be employed in the therapeutic agent. The amount of excipient that is useful in the therapeutic agent is an amount that serves to uniformly distribute the one or more active ingredients throughout the therapeutic agent so that the active ingredient can be uniformly dispersed when delivered to a subject in need thereof. The excipient may serve to dilute the active ingredient to a concentration at which the desired beneficial palliative or curative results are obtained, while at the same time minimizing any adverse side effects that might occur from too high a concentration of active ingredient. The excipient may also have a preservative effect. Thus, for an active ingredient that has high physiological activity, more of the excipient will be employed. On the other hand, for an active ingredient that exhibits a lower physiological activity a lesser quantity of the excipient will be employed. In general, the amount of excipient in the composition will be between about 50% weight (w) and 99.9% w. of the total composition. For active ingredients that have particularly high physiological activities, the amount may be between about 98.0% and about 99.9% w.

A "depot" includes but is not limited to capsules, microspheres, particles, gels, coatings, matrices, wafers, pills or other pharmaceutical delivery compositions for containing one or more active ingredients. A depot may comprise a biopolymer. The biopolymer may provide for non-immediate release of the one or more active ingredients. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof.

"Localized" delivery is defined herein as non-systemic delivery in which a therapeutic agent is deposited within a tissue, for example the disc 20, or in close proximity (within about 10 cm, or preferably within about 5 cm, for example) thereto, such as within the disc region 25. A "controlled administration system" provides localized delivery of one or more active ingredients in a quantity of therapeutic agent that can be deposited at the target site as needed for pain, either continuously or at an intermittent rate. A "controlled administration system" includes, but is not limited to, a bolus of the therapeutic agent, a depot, an osmotic pump, an interbody pump, an infusion pump, implantable mini-pumps, a peristaltic pump, other pharmaceutical pumps, or a system administered locally by insertion of a catheter into, at or near a disc, the catheter being operably connected to a pharmaceutical delivery pump. It is understood that pumps can be internal or external as appropriate.

In a first embodiment, the therapeutic agent comprises at least one active ingredient that disrupts neuronal elements in the disc region 25 by destroying, forcing retraction or blocking the further growth of the neuronal elements in the disc region 25. The active ingredient may target one or more aspects of the neuronal elements to achieve this disruption, some of which are indicated in the following.

For example, in one variation of the first embodiment, the therapeutic agent comprises an active ingredient that is a neurotoxin. Suitable neurotoxins may be found in nature, such as neurotoxins that are isolated from invertebrates, reptiles, marine animals, plants or microorganisms. Alternatively, the neurotoxin may be a synthetic compound; specifically, compounds comprising ammonia or cyamide may be suitable as a neurotoxic active ingredient. Or, the neurotoxin may be a dye, such as bisbenzimide, trypan blue, brilliant blue, methylene blue, indocyanine green, ruthenium red or quinoline yellow. Particularly suitable neurotoxins are the cell membrane-permeabilizing agents like the saponins, which may advantageously be linked to a molecule that binds to, or is incorporated by, the neuronal elements 28. As such, a saponin molecule, for example a saporin may be targeted at the neuronal elements. Exemplary molecules to which saporin may be linked include neurotransmitters, neuropeptides, growth factors, antibodies capable of interacting with the neuronal elements 28, or peptides capable of interacting with the neuronal elements 28. Allen et al., for example, disclose intrathecal substance P-Saporin (SP-SAP) that selectively destroys superficial neurokinin 1 receptor (NK1r)-bearing cells. See Jeffery W. Allen et al., *Safety Evaluation of Intrathecal Substance P-Saporin, a Targeted Neurotoxin, in Dogs,* 91(1) TOXICOLOGICAL SCIENCES 286-98 (2006).

In another variation of the first embodiment, the therapeutic agent may modulate a growth factor, or modulate the response of the neuronal elements 28 to a growth factor. Exemplary growth factors include nerve growth factor, brain-derived growth factor, glial-derived growth factor, neurotrophin-3, neurotrophin-4, insulin-growth factor, fibroblast growth factor and leukemia inhibitory factor. As an example of a suitable active ingredient that may achieve this disruption of a growth factor, neutralizing antibodies delivered locally or slowly released from a matrix, such as a collagen matrix, can significantly disrupt growth of neuronal extensions 18. See Streppel M. Azzolin et al., *Focal application of neutralizing antibodies to soluble neurotrophic factors reduces collateral axonal branching after peripheral nerve lesion,* 15(8) EUR. J. NEUROSC. 1327-42 (2002). ReN-1820, which may also be a suitable active ingredient, is a recombinant protein that contains the binding domain of the NGF protein and acts as a soluble receptor to the endogenous NGF protein, thus reducing the levels of NGF that can bind to NGF receptors found on neuronal elements. ALE-0540, which may also be a suitable active ingredient, is an NGF receptor antagonist that can reduce pain and inflammation. See J. B. Owolabi et al., *Characterization of antiallodynic actions of ALE-0540, a novel nerve growth factor receptor antagonist, in the rat,* 289(3) J. PHARMACOL. EXP. THER. 1271-76 (1999).

In yet another variation of the first embodiment, the therapeutic agent may modulate an extra-cellular matrix component, or modulate the response of the neuronal elements 28 to an extra-cellular matrix component. Exemplary extra-cellular matrix components include chondroitin sulfate proteglycans; netrins; semaphorins; and myelin/oligodendrocyte growth inhibitors, such as Nogo, MAG and OMgp. Alternatively, the extra-cellular matrix component may be a cell adhesion molecule, such as NCAM, N-cadherins and integrins. Factors that interfere with cell adhesion molecules can induce detachment and retraction of neuronal extensions and/or neuronal death, and hence may serve as suitable active ingredients in a therapeutic agent. See C. Bozzo et al., *Soluble integrin ligands and growth factors independently rescue neuroblastoma cells from apoptosis under nonadherent conditions,* 237(2) EXP. CELL RES. 326-37 (1997).

In yet another variation of the first embodiment, the therapeutic agent may modulate a cytoskeletal component, or may modulate the organization of established or actively growing neuronal elements 28. Exemplary cytoskeletal components include actins, tubulins or neurofilaments, and an exemplary active ingredient for the therapeutic agent includes a Rho kinase activator. Cytotoxic necrotizing factor-1 and -2 from *E. coli* are Rho kinase activators and have been shown to modulate the organization of the actin cytoskeleton and induce retraction of neuronal extensions and shortening of axons, and may serve as suitable active ingredients. See S. Boutillier et al., *Cytotoxic necrotizing factor-2 of Escherichia coli alters the morphology of cultured hippocampal neurons,* 368(6) NAUNYN SCHMIEDEBERGS ARCH PHARMACOL. 513-19 (2003).

In a second embodiment, the therapeutic agent comprises at least one active ingredient that desensitizes the neuronal elements 28 in the disc region 25. In one variation, the active ingredient may be camphor, menthol, piperine, mustard oil, curcumin or eugenol. In another variation, a vanilloid receptor agonist may be employed for the active ingredient, such as such as 8-Methyl-N-vanillyl-trans-6-nonenamide (Capsaicin); Z-Capsaicin; Gingerol; Zingerone; 8-Methyl-N-vanillylnonanamide (Dihydrocapsaicin); 6,7-Deepoxy-6,7-didehydro-5-deoxy-21-dephenyl-21-(phenylmethyl)-daphnetoxin,20-(4-hydroxy-5-iodo-3-methoxybenzeneacetate) (5'-Iodoresiniferatoxin)-?; (+)-Isovelleral; N-Vannilyloleoylamide (Olvanil); Phorbol 12,13-dinonanoate 20-homovanillate; Resiniferatoxin; N-(3-Methoxyphenyl)-4-chlorocinnamide (SB-366791); 2,3,4-Trihydroxy-6-methyl-5-[(2E,6E)-3,7,11-trimethyl-2,6,10-dodecatrienyl]benzaldehyde (Scutigeral); 6,7-Deepoxy-6,7-didehydro-5-deoxy-21-dephenyl-21-(phenylmethyl)-20-(4-hydroxybenzeneacetate)daphnetoxin (Tinyatoxin); capsaicin synthetics; and capsaicin derivatives.

It will be appreciated that active ingredients employed for the first embodiment may also be employed in the second embodiment. Hence, the second embodiment therapeutic agent may comprise one or more active ingredients that destroy, force the retraction or block the further growth of neuronal elements 28 in the disc region 25; and one or more active ingredients that desensitize the neuronal elements 28 in the disc region 25.

In a third embodiment, the therapeutic agent may modulate the neuronal elements 28 in the disc region 25. More specifically, the therapeutic agent may modulate the activity of the neuronal elements 28 in the disc region 25. In one variation, the therapeutic agent modulates the sensitivity of neuronal receptors, such as nociceptors, vanilloid, adrenergic, cholinergic, glutamate, GABA, serotonine, somatostatin opioids, ATP, Na+, K+, Ca2+, cannabinoids, Substance P and neuropeptide receptors. Suitable active ingredients in this variation includes botulinum toxin, anti-convulsants, anesthetics, analgesics, opioids and cannabinoids. In another variation, a vanilloid receptor antagonist is used for the active ingredient; exemplary compounds for the active ingredient include N-[2-(4-Chlorophenyl)ethyl]-1,3,4,5-tetrahydro-7,8-dihydroxy-2H-2-benzazepine-2-carbothioamide (Capsazepine); [N-(4-Hydroxy-3-methoxyphenyl) methyl]-5Z,8Z,11Z,14Z-eicosatetraenamide] (Arvanil); N-(3-Methoxyphenyl)-4-chlorocinnamide (SB-366791) and 5'-iodoresiniferatoxin.

It will be appreciated that active ingredients employed for the first and second embodiments may also be employed in the third embodiment. Hence, the third embodiment therapeutic agent may further comprise one or more active ingredients that destroy, force the retraction or block the further growth of neuronal elements 28 in the disc region 25; and/or one or more active ingredients that desensitize the neuronal elements 28 in the disc region 25. Similarly, active ingredients employed in the third embodiment therapeutic agent may also be used in the first and second embodiment therapeutic agents.

In a fourth embodiment, the therapeutic agent may disrupt the neuronal elements 28 by causing reduction in the sensitization of the neuronal elements 28 by a pro-inflammatory molecule. Exemplary pro-inflammatory molecules that may be targeted include cytokines, chemokines, neuropeptides, bradykinin, histamine and prostaglandins. Suitable active ingredients for the therapeutic agent include steroids, nonsteroidal anti-inflammatory drugs, COX inhibitors, modulators of TNF-alpha or IL-1 cytokine levels or receptors, or NFkB modulators.

As previously indicated, any one or more of the prior embodiment active ingredients may also be incorporated into the fourth embodiment therapeutic agent. Similarly, active ingredients associated with the fourth embodiment therapeutic agent may also be incorporated into any of the previous embodiment therapeutic agents. Hence, a fourth embodiment therapeutic agent may include a first active ingredient that reduces the sensitization of the neuronal elements 28 to a pro-inflammatory molecule; a second active ingredient that destroys, causes the retraction of or blocks further growth of the neuronal elements 28, and a third active ingredient that desensitizes the neuronal elements 28.

In a fifth embodiment, the neuronal elements 28 specifically targeted for disruption are glial cells. A fifth embodiment therapeutic agent comprises an active ingredient that modulates the glial cells, which may include destroying the glial cells; hence, in one variation, the fifth embodiment therapeutic agent comprises an active ingredient that is toxic to glial cells. The fifth embodiment therapeutic agent is not, however, limited to merely destroying the glial cells, but may also modulate the number or activity of the glial cells. For example, the fifth embodiment therapeutic agent may modulate the level of, or glial cell response to, fibroblast growth factor; or, the fifth embodiment therapeutic agent may modulate the number or activity of glial purinergic, cytokine, chemokine, neuropeptide or glutamate receptors. In a particular variation, the fifth embodiment therapeutic agent comprises minocyclin or fluorocitrate as an active ingredient. Any of the previous embodiment active ingredients may be further incorporated into the fifth embodiment therapeutic agent; similarly, active ingredients associated with the fifth embodiment therapeutic agent may be incorporated into any of the previous embodiment therapeutic agents.

In a sixth embodiment, a therapeutic agent may comprise, alone or in combination with any of the prior embodiment active ingredients, an active ingredient that disrupts vascular elements 29 in the disc region. The active ingredient within the sixth embodiment therapeutic agent may include, for example, an anti-angiogenic agent, or saporin. Suitable anti-angiogenic agents include, for example, thalidomide, Neovastat (AE-941) and Rh endostatin. As previously indicated, a cell membrane-permeabilizing agent, for example, saporin is particularly useful in that it can be linked to a molecule that binds to, or is incorporated by, the vascular elements 29, thus providing for targeted delivery of the saporin to the vascular elements 29. Molecules to which saporin may be linked include, for example, growth factors, or an antibody or peptide that interacts with the vascular elements 29. For example, the anti-angiogenic potential of saporin linked to FGF has been explored. See D. A. Lappi et al., *Biological and chemical characterization of basic FGF-saporin mitotoxin,* 160(2) BIOCHEM. BIOPHYS. RES. COMMUN. 917-23 (1989). In another variation, the active ingredient may disrupt the vascular elements 29 by modulating a growth factor or cytokine, or the response of the vascular elements 29 to a growth factor or cytokine; exemplary growth factors or cytokines include vascular growth factor, fibroblast-growth factor, angiopoietins, pigment epithelium-derived factor and α-IFN. In yet another variation, the active ingredient may comprise an inhibitory antibody, an aptamer, or a soluble fragment of a growth factor or growth factor receptor; exemplary active ingredients include bevacizumab, pegaptanib and ranibizumab. In still another variation, the sixth embodiment active ingredient may comprise an anti-angiogenic steroid or an angiostatic steroid, such as anecortave acetate or triamcinolone acetonide. In a further variation, the active ingredient may modulate an extra-cellular matrix component, or the response of the vascular elements 29 to an extra-cellular matrix component; the extra-cellular matrix component may be an MMP inhibitor, such as marimastat; alternatively, the extra-cellular matrix component may be cell adhesion molecules, such as cadherins or integrins. Or, for yet another variation, the active ingredient may modulate a cytoskeletal component of established or actively growing vascular extensions 29, such as microtubules; exemplary active ingredients include combretastatin, vinca alkaloid or placlitaxel.

In a seventh embodiment, the therapeutic agent may modulate the response of a vascular element 29 to pro-inflammatory molecules. Exemplary pro-inflammatory molecules that may be targeted include cytokines, chemokines, neuropeptides, bradykinin, histamine and protaglandins. Suitable active ingredients for the therapeutic agent include steroids, nonsteroidal anti-inflammatory drugs, COX inhibitors, modulators of TNF-alpha or IL-1 cytokine levels or receptors, or NFkB modulators.

As previously indicated, the therapeutic agent may include two or more active ingredients. One of these active ingredients may be designed to disrupt neuronal elements 28, such as the neuronal extensions 18, in the disc region 25, while another active ingredient may be designed to disrupt vascular elements 29, such as the vascular extensions 19, in the disc region 25. Of course, even greater numbers of active ingredients are possible within the therapeutic agent, as would be appreciated by one of skill in the art. Suitable dosing regimens, compositions and delivery methodologies for the therapeutic agent are ideally determined by a skilled medical practitioner.

A preferred mode of delivery achieves a local accumulation of the therapeutic agent in the disc 20. It is anticipated that localized delivery may be desirable to avoid, or minimize, side-effects, and to target extensions or elements within specific regions. Generally, the therapeutic agent may be designed to disrupt vascular and/or neuronal elements in the entire disc. Alternatively, the therapeutic agent may be designed and administered to target such elements within the interior regions of the disc, while leaving largely unaffected those elements in the exterior regions of the disc. The exterior region of the disc may include, for example, the outer one-third of the annular fibrosus and the cartilaginous endplate. The interior regions of the disc may include the interior two-thirds of the annular fibrosus and the nucleus pulposus; more narrowly, the interior region may include the inner third of the annular fibrosus and the nucleus pulposus; more narrowly still, the interior region may simply be the nucleus pulposus.

Figure 6:
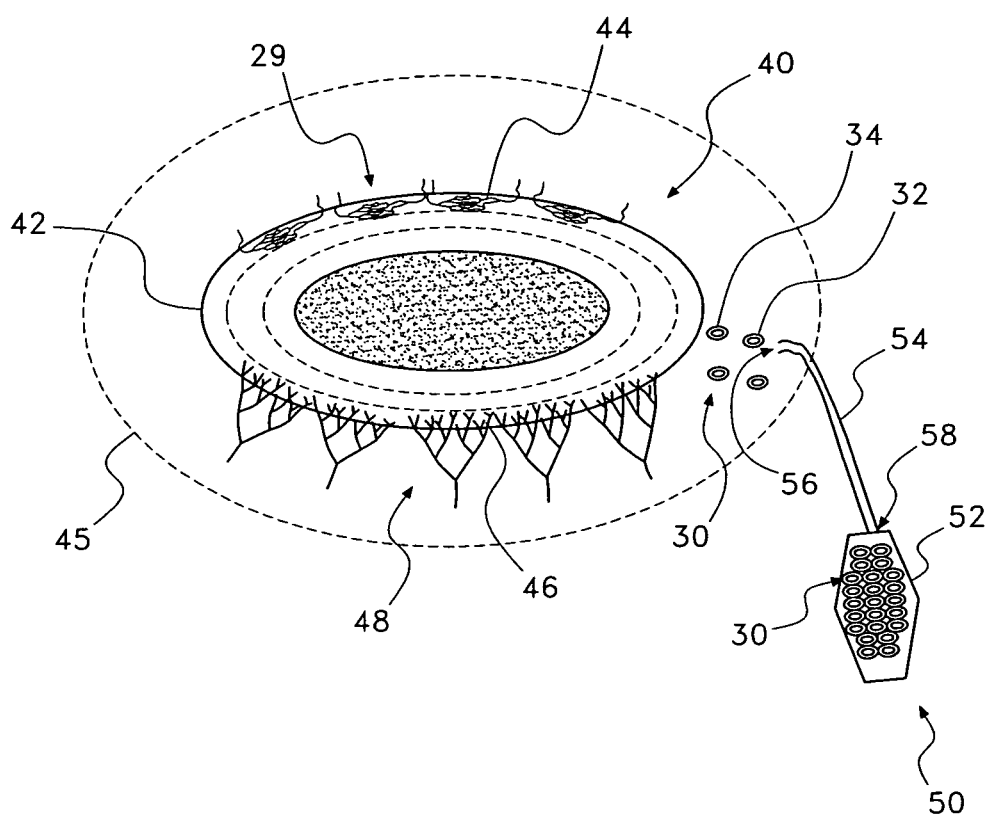
FIG. 6 shows localized delivery of a therapeutic agent with an interbody pump, in which release is near a disc that is to be treated.

In one embodiment, as shown in FIG. 6, localized delivery of an effective amount of a therapeutic agent 30 to a disc 40 can be provided by a controlled administration system 50 comprising an interbody, osmotic pump or similar pharmaceutical pump 52, and an optional catheter 54 fluidly connected to the pump 52 to provide a channel for the therapeutic agent 30 to be transported from the pump 52 to the target disc 40. The pump 52 provides for the controlled release of the therapeutic agent 30 in the disc region 45 at a rate that substantially matches a targeted release rate selected, for example, by a doctor. In certain embodiments, the therapeutic agent 30 may include at least one modified release pharmaceutical carrier 32 for at least one active ingredient 34 in the therapeutic agent 30. The modified release pharmaceutical carrier 32 may, for example, encapsulate the active ingredient 34 to provide timed release of the active ingredient 34. As shown, a distal end 56 of the catheter 54 may terminate within the disc region 45, such as within 5 cm or less of the outer surface 42 of the disc 40; the therapeutic agent 30 is thus directly released into the disc region 45 to target the disc 40. The proximal end 58 of the catheter 54 is fluidly connected to the pump 52. The therapeutic agent 30 may be designed to disrupt one or more of the neuronal elements 48 or vascular elements 49 in the disc 40 or disc region 45, such as the neuronal extensions 46 in the disc 40, or the vascular extensions 44 in the disc 40, as has been indicated earlier. The implantable pump 52 may be positioned elsewhere in the body, or externally to the body, and provided with one or more catheters 54 to deliver the therapeutic agent 30 to appropriate sites in the spine. Implantation can occur simultaneously with surgery to repair a fracture, remove a tumor, etc., or can be performed in individuals who experience pain, especially chronic pain, as the result of earlier trauma, injury, surgery, or other initiation of discogenic pain.

Figure 7:
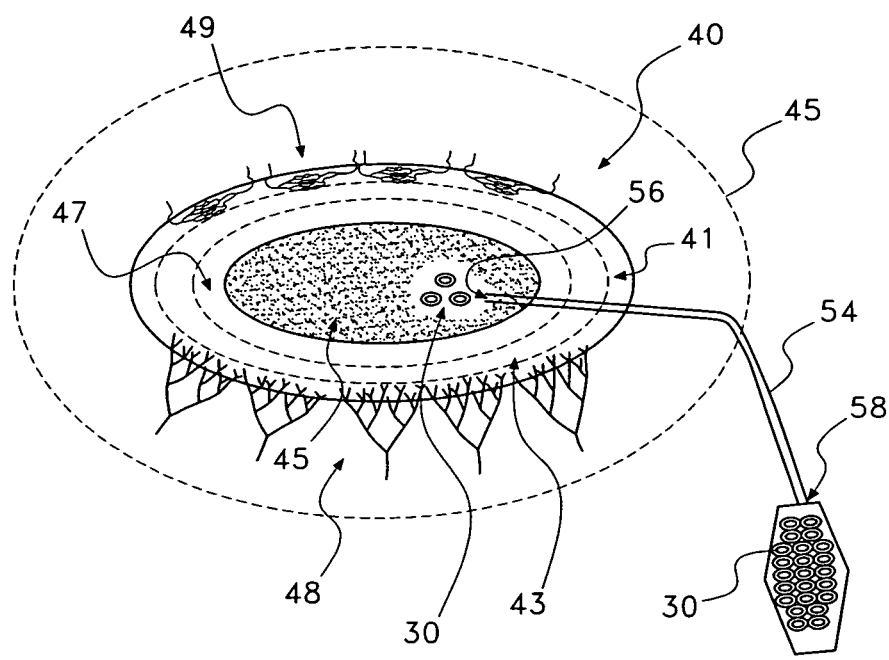
FIG. 7 shows localized delivery of a therapeutic agent with an interbody pump, in which release is within a disc that is to be treated.

In another embodiment, as shown in FIG. 7, the distal end 56 of the catheter 54 may terminate inside the disc 40, such as within the inner two-thirds 43 of the annulus fibrosus or within the nucleus pulposus 45, so that the therapeutic agent 30 is released inside the disc 40. The proximal end 58 of the catheter 54 is fluidly connected to the pump 52. The therapeutic agent 30 may be designed to disrupt neuronal elements 48 in the disc 40, vascular elements 49 in the disc 40, or both. It is anticipated that by careful controlling of the dosage and release rates of the therapeutic agent 30, disruption of neuronal elements 48 and/or vascular elements 49 within the disc region 45 may be obtained with minimal disruption of these elements 48, 49 outside of the disc region 45.

The controlled administration system 50 of the invention may include, for example, an infusion pump that administers the therapeutic agent 30 through catheter 54 near the spine or one or more degenerated discs, an implantable mini-pump that can be inserted at the target site, an implantable controlled release device (such as, for example, the device described in U.S. Pat. No. 6,001,386), or a sustained release delivery system (such as the system described in U.S. Pat. No. 6,007,843). The administration system 50 may provide targeted release rates of the therapeutic agent 30 so as to control dosage levels as a function of time. Here, and in the following, the targeted release rate should be one which provides pharmaceutically effective amounts of the active ingredient so as to cause the desired disruption of the targeted neuronal elements 48 and/or vascular elements 49 in the disc 40 or disc region 45, as determined by, for example, a physician. An effective treatment could also be one that leads to a better outcome for patients affected by neck and/or back pain.

One example of a suitable pump is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the therapeutic agent is injected through the reservoir fill port to the expandable reservoir. The inert gas creates pressure on the reservoir, and the pressure forces the therapeutic agent through a filter and into the pump chamber. The therapeutic agent is then pumped out of the device from the pump chamber and into the catheter, which will direct the therapeutic agent to the target site, i.e., within or near the disc. The rate of delivery of the therapeutic agent is controlled by a microprocessor. This allows the pump to be used to deliver similar or different amounts of the therapeutic agent continuously, at specific times, or at set intervals between deliveries, thereby controlling the release rates to correspond with the desired targeted release rates.

Potential drug delivery devices suitable for adaptation for the method of the invention include, but are not limited to, those devices found in U.S. Pat. No. 6,551,290 (Elsberry, et al.), which describes a medical catheter for targeted, specific drug delivery; U.S. Pat. No. 6,571,125 (Thompson), which describes an implantable medical device for controllably releasing a biologically-active agent; U.S. Pat. No. 6,594,880 (Elsberry), which describes an intraparenchymal infusion catheter system for delivering therapeutic agents to selected sites in an organism; and U.S. Pat. No. 5,752,930 (Rise, et al.), which describes an implantable catheter for infusing equal volumes of agents to spaced sites.

Additional designs which may be adapted to be employed in the method of the present invention are provided, for example, in United States Patent Applications, such as US 2002/0082583 (a pre-programmable implantable apparatus with a feedback regulated delivery method), US 2004/0106914 (a micro-reservoir osmotic release system for controlled release of chemicals), US 2004/0064088 (a small, light-weight device for delivering liquid medication), US 2004/0082908 (an implantable microminiature infusion device), US 2004/0098113 (an implantable ceramic valve pump assembly), and US 2004/0065615 (an implantable infusion pump with a collapsible fluid chamber). Alzet® osmotic pumps (Durect Corporation, Cupertino, Calif.) are also available in a variety of sizes, pumping rates and durations suitable for use in the method of the present invention.

Figure 8:
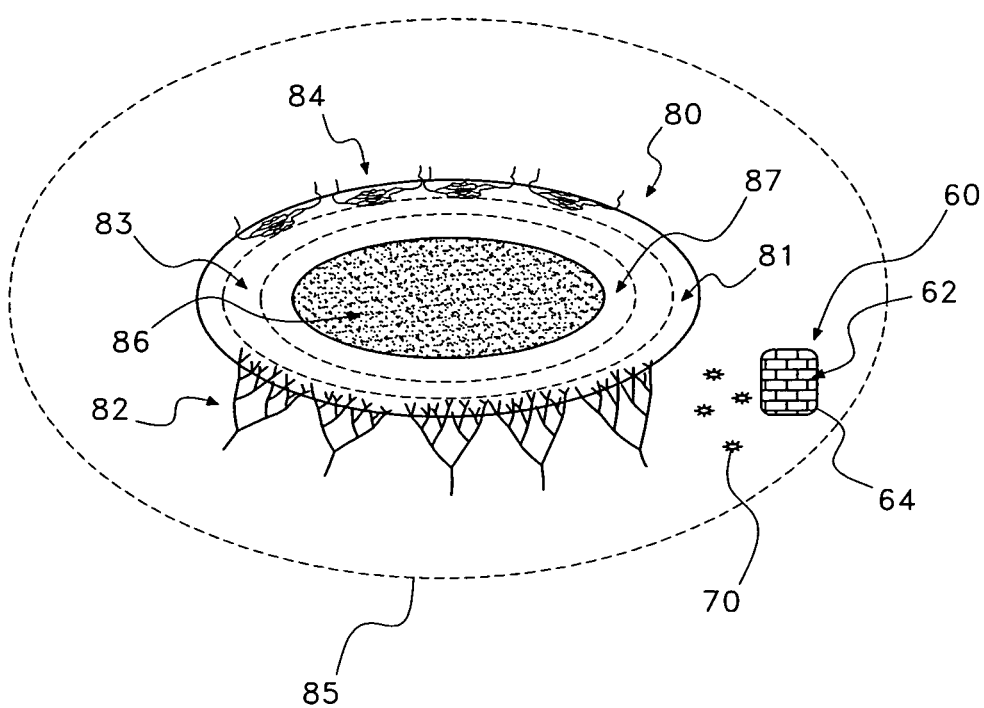
FIG. 8 shows localized delivery of a therapeutic agent with a depot that is disposed near a disc that is to be treated.
Figure 9:
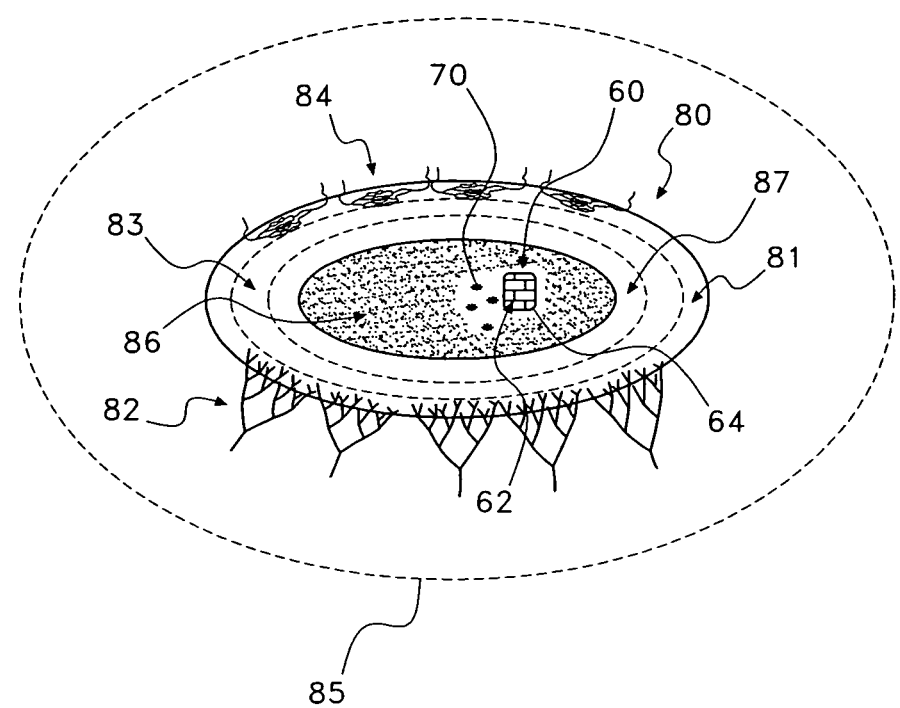
FIG. 9 shows localized delivery of a therapeutic agent with a depot that is disposed within a disc that is to be treated.

In alternative embodiments, as shown in FIGS. 8 and 9, the therapeutic agent may be in the form of a depot 60 that is used to provide local administration of a therapeutically effective amount of at least one active ingredient 70 selected to disrupt neuronal elements 82 and/or vascular elements 84 in a disc 80, or, more broadly, in a disc region 85, to treat discogenic pain. The depot 60 may comprise a polymer matrix 62 that breaks down over time within the tissues, or otherwise incorporates the one or more active ingredients 70 within a protective coating 64 that provides for the delay of the release of the one or more active ingredients 70, thus providing release rates of the active ingredient 70 that follow the desired targeted release rates. As shown in FIG. 7, the depot 60 may be placed close to the disc 80 that is to be treated, and ideally immediately adjacent to, or within 5 cm of, the disc 80. Hence, the depot 60 may be disposed within the disc region 85 to target those elements 83, 84 within the disc 80, or within the disc region 85. As shown in FIG. 9, in an alternative embodiment, the depot 60 may be implanted within the disc 80, such as within the nucleus pulposus 86. The depot 60 may be designed to disrupt neuronal elements 82 and/or vascular elements 84 within the interior regions of the disc 80 with minimal disruption to those elements outside of the disc region 85.

Figure 10:
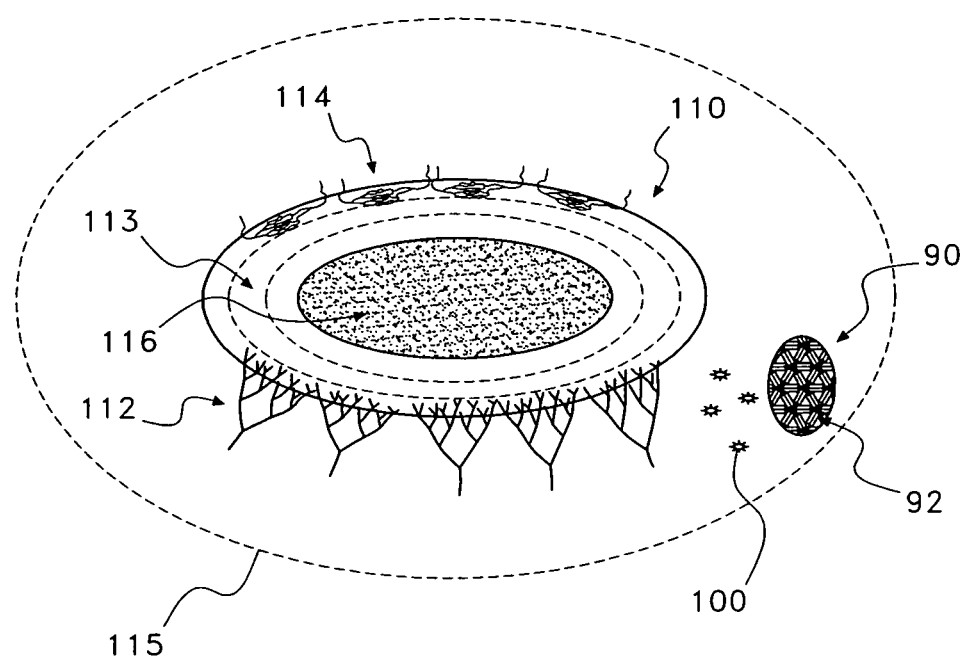
FIG. 10 shows localized delivery of a therapeutic agent with a bolus that is disposed near a disc that is to be treated.
Figure 11:
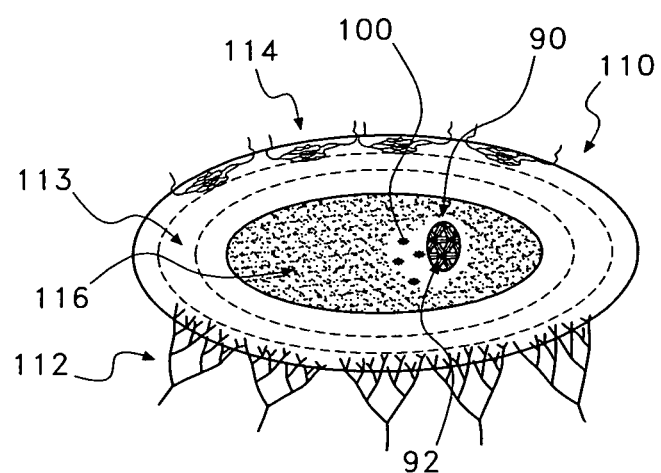
FIG. 11 shows localized delivery of a therapeutic agent with a bolus that is disposed within a disc that is to be treated.

As shown in FIGS. 10 and 11, the therapeutic agent may be in the form of a bolus 90 of microcapsules/microbubbles 92 encapsulating one or more active ingredients 100. The microcapsules/microbubbles 92 provide for timed release of therapeutically effective amounts of the one or more active ingredients 100 that target neuronal elements 112 and/or vascular elements 114 in the disc 110, and more broadly in the disc region 115. The disc 110 may be a source of discogenic pain, such as a degenerated disc. As shown in FIG. 10, the bolus 90 may be disposed within tissue near the disc 110, and in particular may be disposed within the disc region 115; or, as shown in FIG. 11, the bolus 90 may be disposed within the disc 110 itself. Specifically, the bolus 90 may be placed within the interior regions of the disc 110, such as, for example, within the inner two-thirds 113 of the annulus fibrosus, or within the nucleus pulposus 116. Of course, other pharmaceutical carriers other than microcapsules or microbubbles may be employed as carriers for the active ingredients 100, such as injectable gel carriers or mini-rod polymeric delivery devices.

By providing one or more active ingredients at or in close proximity to the disc to be treated, particularly when those active ingredients are provided in a controlled-release manner, the amount of therapeutic agent that must be administered in relation to systemic modes of administration, such as orally or by injection, is decreased. This increases the pharmaceutical efficiency and decreases the rate/severity of systemic side effect(s) of the therapeutic agent, because it is being directed to the targeted tissue.

The above embodiments provide for targeted delivery of the therapeutic agent by way of a controlled administration system, be it a pump, a depot, bolus, etc. Such systems provide for the localized delivery of the therapeutic agent. Although systemic delivery of the therapeutic agent may be possible, it is generally less desirable than localized delivery due to the possibilities of side effects arising from the active ingredients. However, with certain embodiments, it is possible to provide for systemic delivery of the therapeutic agent that selectively targets the desired elements within the disc or disc region.

For example, in one embodiment, the at least one active ingredient may be selectively delivered to a degenerated disc or disc region by conjugating one or more active ingredients to antibodies selectively targeting degenerated discs. As indicated above, this embodiment is especially advantageous for systemic targeted delivery of the at least one active ingredient. For example, it has been known that the concentration of keratan sulfate is increased in damaged or degenerated intervertebral discs. See Kupier et al., 23 SPINE 657-63 (1998). It was further reported that monoclonal antibodies to keratan sulfate specifically target damaged discs. See Kairemo et al., 42(3) J. NUCLEAR MEDICINE 476-81 (2001). Thus, the antibody to a degenerated disc marker, such as, for example, keratan sulfate, the concentration of which is increased in degenerated discs, would deliver the at least one active ingredient to degenerated or damaged discs with a relatively high specificity. A person of ordinary skill in the art would undoubtedly appreciate that multiple ways exist of creating the suitable antibody. These methods are described in detail in multiple patent and non-patent references, including, for example, US 2005/0214822, incorporated herein by reference in its entirety.

A person of ordinary skill would further be able to conjugate the at least one active ingredient to the antibody specifically targeting the degenerated disc. Methods of conjugating the at least one active ingredient are described, for example, in US 2006/0074008, which discloses a Drug-Linker-Ligand conjugation model and is incorporated in its entirety by reference into the instant disclosure. Another method of conjugation is especially suitable for the at least one active ingredient which contains carboxyl groups. These agents can be joined to lysine s-amino groups in the antibodies either by preformed reactive esters (such as N-hydroxy succinimide ester) or esters conjugated in situ by a carbodiimide-mediated reaction, as described in US 2006/0073100, incorporated by reference in its entirety into the instant disclosure.

More generally, the active ingredient may be linked to a molecule that binds to, or is incorporated by, the neuronal or vascular elements that are to be targeted. For example, the active ingredient saporin may be linked to a suitable growth factor, such as FGF, to target a vascular element, or may be linked to Substance P to target a neuronal element. Exemplary molecules to which a suitable active ingredient may be linked include neural or vascular growth factors, antibodies or peptides capable of interacting with the vascular or neural element, neurotransmitters, and neuropeptides. Exemplary active ingredients include cell membrane-permeabilizing agents such as saporin, granulysin and pore-forming polypeptides.

The use of therapeutic agents that are activated by light is also known. See Stanley S. Stylli & Andrew H. Kaye, *Photodynamic therapy of cerebral glioma—A review*, J. CLINICAL NEUROSCIENCE (2006). A photodynamic therapeutic agent may be selected that, when activated by the appropriate frequency of electromagnetic radiation, will disrupt the neuronal or vascular extensions. The therapeutic agent may be administered systemically. Then, the disc region is illuminated by a light source having a suitable intensity and frequency that causes the therapeutic agent to activate. Hence, activation of the therapeutic agent may be contained within the disc region, thereby selectively targeting neuronal or vascular elements in the disc region, and in particular within the disc, without substantially affecting those elements outside the disc region. The light source is typically a laser, and may be delivered to the disc region via an optical fiber, or may be shone through surrounding tissue, such as skin, into the disc region. The therapeutic agent may contain, for example, Aminolevulinic acid, Photofrin, Mono-L-aspartyl chlorine e6, Haematoporphyrin derivative, Purlytin (Tin etiopurpurin), Foscan (temoporfin, mTHPc), Lutetium Texaphyrin, Benzoporphyrin Derivative—Monoacid Ring A (BPDMA), Tetra (m-hydroxyphenyl) chlorine (mTHPC), N-Aspartyl chlorine e6 (NPe6) or phthalocyanines as active ingredients.

Another mode of selectively activating the therapeutic agent within the disc region involves the use of microbubbles. It is known that microbubbles encapsulating the one or more active ingredients may release those active ingredients when subjected to sonic energy. See Alexander L. Klibanov, *Microbubble Contrast Agents: Targeted Ultrasound Imaging and Ultrasound-Assisted Drug-Delivery Applications*, 41 INVEST. RADIOL. 354-62 (2006). The therapeutic agent thus may comprise suitably constructed microbubbles that encapsulate one or more active ingredients. These microbubbles may be administered systemically or locally as warranted. Subsequently, the disc region is subjected to sonic energy that causes the microbubbles to release the one or more active ingredients. The sonic energy is typically ultrasound, and may be delivered, for example, via transducers placed in contact with the skin adjacent to the disc region. Without wishing to be bound by theory, it is believed that the sonic energy causes the microbubbles to rupture or crack, thereby releasing the active ingredients into the surrounding tissue. In this manner, the therapeutic is selectively released into the disc region.

Another method of targeted delivery of the therapeutic agent contemplated by the present invention involves using gene therapy. Gene therapy has recently emerged as a powerful approach to treating a variety of mammalian diseases. Most useful are those retroviruses that are replication-deficient (i.e., capable of directing synthesis of the desired proteins, but incapable of manufacturing an infectious particle). Such genetically altered retroviral expression vectors have general utility for high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are known. See M. KRIEGLER, GENE TRANSFER AND EXPRESSION, A LABORATORY MANUAL (W.H. Freeman Co., New York, 1990) and 7 METHODS IN MOLECULAR BIOLOGY (E. J. Murry e.d., Humana Press, Inc., Clifton, N.J. 1991). Direct transfer of genetic material into neuronal tissue in vivo has recently been demonstrated to be an effective method of expressing a desired protein. For example, direct neuronal gene transfer of DNA encoding active clostridial neurotoxin (toxin's light chain component LC) by viral gene transfer into the rat spinal cord (See Teng et al., 12 Gene Therapy 108-19 (2005)), has been shown to result in expression of enzymatically active clostridial neurotoxin in neurons resulting in synaptic disruption in vivo.

It is believed that the method and system of the present invention has both human medical and veterinary use, being suitable for use in children and adults, as well as in other mammals. In veterinary use, the method of the invention may also be useful for decreasing neck and back pain. The method may be especially beneficial for larger animals such as horses, or smaller domestic pets such as cats and dogs.

A kit may be provided to implement the invention method. The kit may comprise at least one aliquot of at least one therapeutic agent in a package so that the therapeutic agent is provided in sterile form when introduced into the body. The therapeutic agent may be in the form of a depot, or a sufficient amount of an one or more active ingredients in combination with one or more modified release pharmaceutical carriers. Kits can also provide modified release carriers containing active ingredients within them, the modified release carriers being enclosed or partially enclosed within a matrix or containment device for complete or partial containment of the modified release carriers, the matrix or containment device being the therapeutic agent that is then provided in sterile packaging; this therapeutic agent may then be implanted into a target site within the body of a subject in need of therapy.

Various testing models exist that can be used to identify optimal therapeutic agents that disrupt neuronal and/or vascular extensions into the disc or disc region. See, for example, Kjell Olmarker, *Neovascularization and Neoinnervation of Subcutaneously Placed Nucleus Pulposus and the Inhibitory Effects of Certain Drugs,* 30(13) Spine 1501-04 (2005), which presents an animal model where growth of neuronal and vascular extensions could be observed into a fat patch implanted subcutaneously containing nucleus pulposus material. No growth was observed in the fat patch implant only.

For a stab-based model, see James Melrose & Janis Menage, *Increased Nerve and Blood Vessel Ingrowth Associated With Proteoglycan Depletion in an Ovine Anular Lesion Model of Experimental Disc Degeneration,* 27(12) Spine 1278-85 (2002), where the authors showed vascular, neuronal and glial ingrowth into a disc after a stab injury to the disc. One aspect of the present invention provides a modified version of this model, which involves injection of NGF and/or VEGF after the stab injury to accelerate neuronal and/or vascular ingrowth into the disc. Processing times for obtaining a suitable model may therefore be reduced. Once the model is obtained, it may be exposed to one or more active ingredients to test these ingredients for therapeutic efficacy in disrupting neuronal and/or vascular elements within the model.

One aspect of the present invention provides the use of the stab model (with or without injection of NGF or VEGF) in rats, to link neuronal and/or vascular ingrowths into the disc to well-established pain testing methods. Therapeutic agents to be delivered targeting those extensions or elements would be tested in those models for their effects on both the disruption of neuronal/vascular elements and/or on behavioral pain testing.

Another aspect of the invention provides a method of testing the therapeutic efficacy of a treatment comprising administering a test compound to reduce or treat neck or back pain. The method comprises determining if an amount of a pain marker is present in a location inside of or adjacent to a degenerated disc at a first time. Hence, testing for the presence of the pain marker may be made, for example, within the disc, or within the disc region. The "first time" is at a time prior to a first administration of the test compound.

The test compound may then be administered, for example in a manner indicated previously, and subsequently an amount of the pain marker in the location inside of or adjacent to the degenerated disc is determined at a second time. If $M_1$ is the amount of the pain marker measured at the first time, $M_2$ is the amount of the pain marker measured at the second time, and N is the normal range or amount of the pain marker, then the treatment may be deemed therapeutically useful for reducing neck or back pain if $|M_1-N|>|M_2-N|$.

One embodiment of the invention provides that the test compound is capable of destroying neuronal and vascular elements in the degenerated disc.

Another embodiment of the invention provides that the test compound is selected from the group consisting of thalidomide, bevacizumab, marimastat, α-IFN, MMP inhibitors, Neovastat (AE-941) Rh endostatin, netrins, NOGO-derived proteins, myelin-derived proteins, oligodendrocytes-derived proteins, botulinum toxin, anesthetics, Substance P receptor (NK1) antagonists, opioids, α-Adrenoceptor agonists, cannabinoids, cholinergic receptor agonists, GABA agonists, glutamate receptor antagonists, [N-(4-Hydroxy-3-methoxyphenyl)methyl]-5Z,8Z,11Z,14Z-eicosatetraenamide] (Arvanil), 8-Methyl-N-vanillyl-trans-6-nonenamide (Capsaicin), N-[2-(4-Chlorophenyl)ethyl]-1,3,4,5-tetrahydro-7,8-dihydroxy-2H-2-benzazepine-2-carbothioamide (Capsazepine), 8-Methyl-N-vanillylnonanamide (Dihydrocapsaicin), 6,7-Deepoxy-6,7- didehydro-5-deoxy-21-dephenyl-21-(phenylmethyl)-daphnetoxin,20-(4-hydroxy-5-iodo-3-methoxybenzeneacetate) (5'-Iodoresiniferatoxin); (+)-Isovelleral, N-Vannilyloleoylamide (Olvanil), Phorbol 12,13-dinonanoate 20-homovanillate, Resiniferatoxin; N-(3-Methoxyphenyl)-4-chlorocinnamide (SB-366791), 2,3,4-Trihydroxy-6-methyl-5-[(2E,6E)-3,7,11-trimethyl-2,6,10-dodecatrienyl]benzaldehyde (Scutigeral), 6,7-Deepoxy-6,7-didehydro-5-deoxy-21-dephenyl-21-(phenylmethyl)-20-(4-hydroxybenzeneacetate) daphnetoxin (Tinyatoxin), capsaicin synthetics, capsaicin derivatives, antibodies targeting vanilloid receptors, capsaicin, capsaicin derivatives, capsaicin synthetics, piperine, mustard oil, eugenol, NGF antagonists, and any combinations thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for treating back or neck pain with or without radiculopathy wherein the pain is caused by NGF, the method consisting of:
   providing a therapeutic agent consisting of an effective amount of ReN-1820, ALE-0540 and capsaicin encapsulated in a depot comprising microbubbles comprising a protective coating for timed local release and having a polymer comprising polyaspirins or poly(N-isopropylacrylamide) that provides for timed local release; and
   subjecting the microbubbles to sonic energy to release the effective amount of ReN-1820, ALE-0540 and capsaicin to at least an annulus fibrosus region or a nucleus pulposus region of a disc, said ReN-1820 being a soluble receptor to NGF and provided to disrupt a neuronal element in at least the annulus fibrosus region or the nucleus pulposus region of the disc and a vascular element in at least the annulus fibrosus region or the nucleus pulposus region of the disc,
   wherein the depot comprises a pore forming agent comprising polyethylene glycol (PEG) and an excipient in an amount of from 50% to 99.9% by weight based on a total weight of the depot.

2. The method of claim 1, wherein the disc is a degenerated disc.

3. The method of claim 1, wherein ReN-1820 destroys, forces retraction or blocks further growth of the neuronal element or vascular element in at least the annulus fibrosus region of the disc.

4. The method of claim 3, wherein ReN-1820 reduces nerve growth factor (NGF), or the response of the neuronal element or vascular element to the NGF.

5. The method of claim 1, wherein the excipient comprises 98% by weight based on the total amount of the depot.

6. The method of claim 1, wherein the excipient comprises 99.9% by weight based on the total amount of the depot.

7. The method of claim 1, wherein the ALE-0540 reduces pain and inflammation caused by NGF in the at least annulus fibrosus region or the nucleus pulposus region of the disc.

8. The method of claim 1, wherein the disc is a degenerated disc; and the excipient is in the depot in an amount of 99.9% by weight based on the total amount of the depot.

9. A method for treating back or neck pain with or without radiculopathy wherein the pain is caused by NGF, the method consisting of:
   providing a therapeutic agent consisting of an effective amount of ReN-1820, ALE-0540 and capsaicin encapsulated in a depot comprising microbubbles comprising a protective coating for timed local release and having a polymer comprising polyaspirins or poly(N-isopropylacrylamide) that provides for timed local release; and
   subjecting the microbubbles to sonic energy to release the effective amount of ReN-1820, ALE-0540 and capsaicin to at least a nucleus pulposus region of a disc, said ReN-1820 provided to disrupt a neuronal element in at least the nucleus pulposus of the disc and a vascular element in at least the nucleus pulposus of the disc,
   wherein the depot comprises a pore forming agent comprising polyethylene glycol (PEG) and an excipient in an amount of from 98% to 99.9% by weight based on a total weight of the depot.

10. The method of claim 9, wherein the disc is a degenerated disc.

11. The method of claim 9, wherein the ReN-1820 destroys, forces retraction or blocks further growth of the neuronal element or vascular element in at least the nucleus pulposus of the disc.

12. The method of claim 9, wherein the ReN-1820 reduces nerve growth factor (NGF), or the response of the neuronal element or vascular element to the NGF.

13. The method of claim 9 wherein said back and neck pain is caused by spinal compression.

14. A method for treating back or neck pain with or without radiculopathy wherein the pain is caused by NGF, the method consisting of:
   providing an effective amount of at least one active ingredient configured to disrupt a neuronal element in at least the annulus fibrosus region or the nucleus pulposus region of the disc and a vascular element in at least the annulus fibrosus region or the nucleus pulposus region of the disc, the active ingredient consisting of ReN-1820, ALE-0540 and capsaicin encapsulated in microbubbles comprising a protective coating for timed local release;
   conjugating the at least one active ingredient to a monoclonal antibody to keratan sulfate configured to selectively target a degenerated disc; and
   delivering the at least one active ingredient conjugated to the antibody systemically to a patient having back or neck pain via sonic energy such that the microbubbles release the active ingredient.

* * * * *

UNITED STATES PATENT AND TRADEMARK OFFICE
CERTIFICATE OF CORRECTION

PATENT NO. : 9,789,161 B2
APPLICATION NO. : 11/414689
DATED : October 17, 2017
INVENTOR(S) : Roy et al.

Page 1 of 1

It is certified that error appears in the above-identified patent and that said Letters Patent is hereby corrected as shown below:

In the Specification

In Column 4, Line 36, delete "keratin" and insert -- keratan --, therefor.

In Column 5, Line 35, delete "fibrosis" and insert -- fibrosus --, therefor.

In Column 6, Line 24, delete "fibrosis" and insert -- fibrosus --, therefor.

In Column 6, Line 25, delete "fibrosis" and insert -- fibrosus --, therefor.

In Column 8, Line 37, delete "(PG)," and insert -- (PGA), --, therefor.

In Column 9, Line 9, delete "cyamide" and insert -- cyanide --, therefor.

Signed and Sealed this
Eighteenth Day of September, 2018

Andrei Iancu
*Director of the United States Patent and Trademark Office*